(12) United States Patent
Mehra et al.

(10) Patent No.: US 7,951,137 B2
(45) Date of Patent: May 31, 2011

(54) METHOD AND SYSTEM FOR TERMINATING AN ATRIAL ARRHYTHMIA

(75) Inventors: Rahul Mehra, Stillwater, MN (US); George J. Klein, London (CA); Michael R. Ujhelyi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1529 days.

(21) Appl. No.: 11/244,764

(22) Filed: Oct. 6, 2005

(65) Prior Publication Data

US 2006/0069410 A1 Mar. 30, 2006

Related U.S. Application Data

(62) Division of application No. 10/059,824, filed on Jan. 30, 2002, now Pat. No. 6,968,226.

(51) Int. Cl.
*A61K 9/22* (2006.01)
*A61N 1/00* (2006.01)
*A61B 5/04* (2006.01)
(52) U.S. Cl. .............. 604/890.1; 607/3; 607/9; 600/516
(58) Field of Classification Search .............. 604/890.1; 600/509, 515–516, 518; 607/3, 9, 14
See application file for complete search history.

(56) References Cited

U.S. PATENT DOCUMENTS 5,560,370 A * 10/1996 Verrier et al. ............... 600/518
5,690,682 A * 11/1997 Buscemi et al. ............... 607/3

* cited by examiner

*Primary Examiner* — Mark W Bockelman
(74) *Attorney, Agent, or Firm* — Michael C. Soldner

(57) ABSTRACT

A method and system is provided for responding, from internally within a patient, to an atrial arrhythmia in a heart including measuring from within the patient at least one electrocardiogram characteristic indicative of the atrial arrhythmia, and controlling from within the patient drug therapy delivery to the patient responsive to measuring the at least one electrocardiogram characteristic. Drug therapy is initiated to the patient responsive to measuring the at least one electrocardiogram characteristic. According to one aspect of the present invention, the drug therapy is staged within the patient prior to measuring the at least one electrocardiogram characteristic. According to another example embodiment, the heart is paced from within the patient at a predefined rate responsive to measuring the at least one electrocardiogram characteristic, pacing occurring alone, or in combination with drug therapy.

35 Claims, 2 Drawing Sheets

METHOD AND SYSTEM FOR TERMINATING AN ATRIAL ARRHYTHMIA

This application is a divisional of application Ser. No. 10/059,824, filed Jan. 30, 2002, now U.S. Pat. No. 6,968,226.

FIELD OF THE INVENTION

The present invention relates to terminating atrial and ventricular fibrillations. In particular, the invention relates to terminating atrial fibrillation while preventing the occurrence of ventricular proarrhythmia (i.e., irregular ventricular rhythm).

BACKGROUND OF THE INVENTION

Cardiac signals are used to measure the health of a patient's heart muscle and are typically obtained from patients by physicians using electrocardiogram (ECG) tracings. FIG. 1 illustrates a portion of an ECG tracing of two complete cycles of the cardiac signal. Each cardiac signal comprises five major signal portions that are identified respectively as the P, Q, R, S and T waves. The P wave represents electrical depolarization of the atrium. The Q wave represents the initial stages of ventricle depolarization and the R wave represents the peak of the depolarization of a ventricular myocardium. The S wave represents the final stages of ventricular depolarization and the T wave represents ventricular repolarization. The QRS complex of the ventricle generally masks atrial repolarization. Under conditions of normal cardiac activity, the R wave represents the conducted sinus beat of the heart. The interval between each apex of consecutive R waves represents the heart period in units of time, with the heart rate being the reciprocal of the RR interval expressed as beats per minute.

FIG. 1 further illustrates a normal cardiac signal labeled with two Q-T intervals, $Q-T_1$ and $Q-T_2$. Each Q-T interval is usually measured from the beginning of the Q wave to the end of the T wave. Studies indicate that the duration of the Q-T interval may be an indicator of cardiac electrical abnormalities. A prolonged Q-T interval, under certain conditions, can indicate a risk of sudden cardiac arrest. Electrical heterogenerty is a substrate for ventricular arrhythmia. A prolonged Q-T interval can also indicate that a ventricular arrhythmia (i.e., an irregular heartbeat or rhythm) in the patient's heart may be imminent. Left cardiac arrest. Electrical heterogenerty is a substrate for ventricular arrhythmia. A prolonged Q-T interval can also indicate that a ventricular arrhythmia (i.e., an irregular heartbeat or rhythm) in the patient's heart may be imminent. Left untreated, sustained ventricular arrhythmia can detrimentally impact a patient's health.

Implanted medical devices exist today that are capable of detecting and treating arrhythmia of a patient. In one example, the implanted medical device includes a defibrillator that applies an electrical therapy to a patient's heart upon detecting an atrial fibrillation. Cardioverters or defibrillators discharge relatively high energy electrical shocks across cardiac tissue to arrest a life threatening atrial or ventricular fibrillation that is detected by the implanted medical device. Defibrillation shocks, while highly effective at arresting the fibrillation, may cause considerable patient discomfort.

Accordingly, there is a need for a method for terminating an arrhythmia that will not cause patient discomfort, the effectiveness of which can be easily verified by analyzing the patient's cardiac signal. An approach that addresses the aforementioned problems, as well as other related problems, is therefore desirable.

SUMMARY OF THE INVENTION

According to one example embodiment, a method of responding, from internally within a patient, to an atrial arrhythmia in a heart includes measuring from within the patient at least one electrocardiogram characteristic indicative of the atrial arrhythmia, and controlling from within the patient drug therapy delivery to the patient responsive to measuring the at least one electrocardiogram characteristic. Drug therapy is initiated to the patient responsive to measuring the at least one electrocardiogram characteristic. According to one aspect of the present invention, the drug therapy is staged within the patient prior to measuring the at least one electrocardiogram characteristic.

According other example embodiments of the present invention, the heart is paced from within the patient at a predefined rate responsive to measuring the at least one electrocardiogram characteristic. Pacing may occur alone, or in combination with drug therapy delivery.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
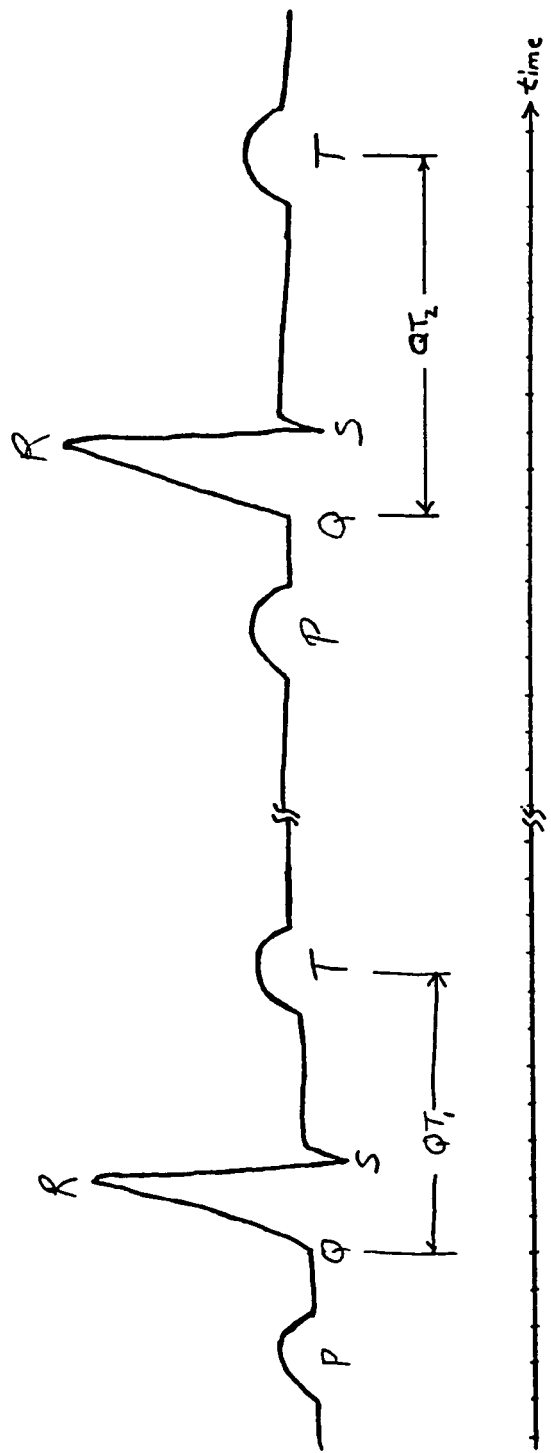
FIG. 1 illustrates an electrocardiogram (ECG) tracing with cardiac activity.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a method and a system for automatic intervention by an implanted device to prevent and/or terminate an atrial arrhythmia in a patient's heart using pacing and/or pharmaceutical therapies. The safety of each therapy is gauged by monitoring whether the therapy triggers conditions in the patient that incite a ventricular arrhythmia (irregular ventricle rhythm). In particular, a patient's cardiac signals, such as those illustrated in the ECG tracing of FIG. 1, provide real-time indications of conditions indicative of the potential safety of a therapy, for example a pharmaceutical or drug therapy. While the present invention is not necessarily limited to such pacing and/or drug therapy applications, the invention will be better appreciated using a discussion of example embodiments in such a specific context.

Various embodiments of the present invention are directed to an implantable medical device (IMD) that routinely monitors cardiac electrical signals to determine, then react responsively to, conditions predictive of an impending ventricular arrhythmia. According to one example embodiment, the IMD monitors conditions of Q-T interval, Q-T dispersion and ventricular ectopy (premature heartbeats), the IMD making comparisons of the measurements to predetermined thresholds and selecting an operating mode responsive to the comparisons.

According to one example embodiment, the IMD automatically initiates ventricular overdrive pacing in an attempt to prevent ventricular proarrhythmia responsive to the comparisons. According to another example embodiment, the IMD automatically initiates ventricular overdrive pacing in an attempt to prevent ventricular proarrhythmia responsive to comparisons made following initiations of drug therapy.

According to a further example embodiment of the present invention, monitoring and pacing continue beyond onset of a ventricular proarrhythmia event. According to various implementations, post-event IMD monitoring continues using pre-event thresholds, new thresholds, or some combination thereof as is applicable to the particular cardiac signal being measured in a particular installation.

According to a further example embodiment of the present invention, in addition to reacting responsively to monitored cardiac signals by pacing, the IMD reacts responsively addressing various needs in connection with administering anti-arrhythmic drugs to a patient to prevent and/or terminate atrial fibrillation while monitoring a patient's cardiac signals to predict and/or detect an onset of ventricular proarrhythmia. Drug therapy initiation/termination thresholds may be the same or different than thresholds established for the initiation/termination of pacing operations, and drug therapy termination thresholds may be different than drug therapy initiation thresholds. The IMD monitors routinely monitors cardiac signals for conditions including, but not limited to, Q-T interval prolongation, Q-T interval variability and a high frequency of ventricular ectopy as indicators that conditions exist for the onset of ventricular arrhythmia and that drug therapy should be terminated.

According to another example embodiment of the present invention, the IMD automatically initiates a course of drug therapy without ventricular overdrive pacing in an attempt to prevent ventricular proarrhythmia responsive to the comparisons. Cardiac signal monitoring continues after initiation of the drug therapy, and drug therapy discontinued should conditions be detected predictive or indicative of an onset of ventricular proarrhythmia.

According to one example implementation including pharmaceutical therapies, the pharmaceuticals are staged outside a patient's body at the time conditions are detected that result in pharmaceutical delivery to the patient. According to another example implementation, the pharmaceuticals are staged inside a patient's body (but within a container isolating the drugs from the patient's body) at the time conditions are detected that result in pharmaceutical delivery to the patient.

The method for terminating an atrial arrhythmia using drug therapy includes pacing a ventricle of the heart at a predefined rate in response to conditions indicative of the atrial arrhythmia and, while pacing the ventricle but before the patient receives the drug therapy, actively measuring at least one Q-T interval of the heart. The method also includes delivering a drug therapy to the patient responsive to measuring the Q-T interval within predetermined duration limits, and preventing drug therapy delivery responsive to measuring the Q-T interval outside of a selected duration range (i.e., excessively long duration). The Q-T interval is further measured during a drug delivery therapy for comparison with the pacing Q-T interval. Q-T intervals that begin to increase in duration during drug therapy, and exceed a predetermined duration from the pacing Q-T interval, terminates the drug therapy to avoid triggering ventricular arrhythmia.

In a further related example embodiment, Q-T interval variability is used as a measure of safety of the drug therapy on terminating the atrial fibrillation. Time variations between individual Q-T intervals over a number of set time periods or set heartbeats indicate that Q-T interval variability is occurring and that the drug therapy is to be terminated to avoid triggering more serious heart conditions. Variability in Q-T intervals is measured before and after delivering a drug therapy. Drug therapy is terminated where Q-T intervals continue to vary, from one interval to another, and exceed a selected threshold Q-T interval variability.

In a related further example embodiment of the invention, in addition to using Q-T interval variability as a cardiac signal indicator of the effectiveness of the drug therapy in preventing and/or terminating an atrial fibrillation, a frequency of ventricular ectopy is measured before and after drug delivery. An increase in the frequency is used as a criteria for termination of the drug therapy.

In another example embodiment, drug therapy safety in terminating the atrial fibrillation is measured using the variation in the frequency of ventricular ectopy after drug therapy with respect to the frequency of ventricular ectopy occurring in a set time period before drug therapy. Drug therapy is terminated where the monitored frequency of ventricular ectopy exceeds a selected threshold level.

As indicated previously, one example embodiment of the present invention uses the monitoring methods for predicting ventricular arrhythmia described to schedule automatic countertherapies (e.g., heart pacing operations) in the absence of any pharmaceutical therapy. When monitored cardiac characteristics meet certain threshold values, the implanted system initiates or discontinues pharmaceutical therapy if relevant, and initiates or discontinues pacing at an overdrive rate if relevant to a particular installation. This automatic intervention by an implanted device is in an attempt to thwart impending ventricular arrhythmia.

Referring again to FIG. 1, the active cardiac signal 100 represented in the electrocardiogram (ECG) tracing is useful in monitoring the effectiveness of drug therapy in terminating an atrial fibrillation. A patient's cardiac signal provides a physician with immediate feedback on the effects of a particular drug therapy that is administered or delivered to the patient either intravenously, intramuscularly, orally, nasally (spray, mask or misting bottle), occularly, transcutaneously or via an internal infusion device.

In describing the various cardiac signal indicators of drug therapy effectiveness, reference is made to FIG. 1. Q-T interval prolongation in the patient occurs where the duration of interval Q-T$_2$ is greater than the duration interval Q-T. The likelihood of an onset of ventricular arrhythmia increases with prolongation of the duration of Q-T intervals over time.

Q-T interval variability in the patient occurs whenever the duration of Q-T intervals, measured over a select time period, consistently vary and are not stable. As Q-T interval variability continues over the select period of time, the likelihood of an onset of ventricular arrhythmia increases.

As discussed above, the high frequency of ventricular ectopy in the patient in a select period of time provides an indication that the conditions exist for the onset of ventricular arrhythmia. Reference will be made to FIG. 1 as the present invention is described further in FIG. 2.

Figure 2:
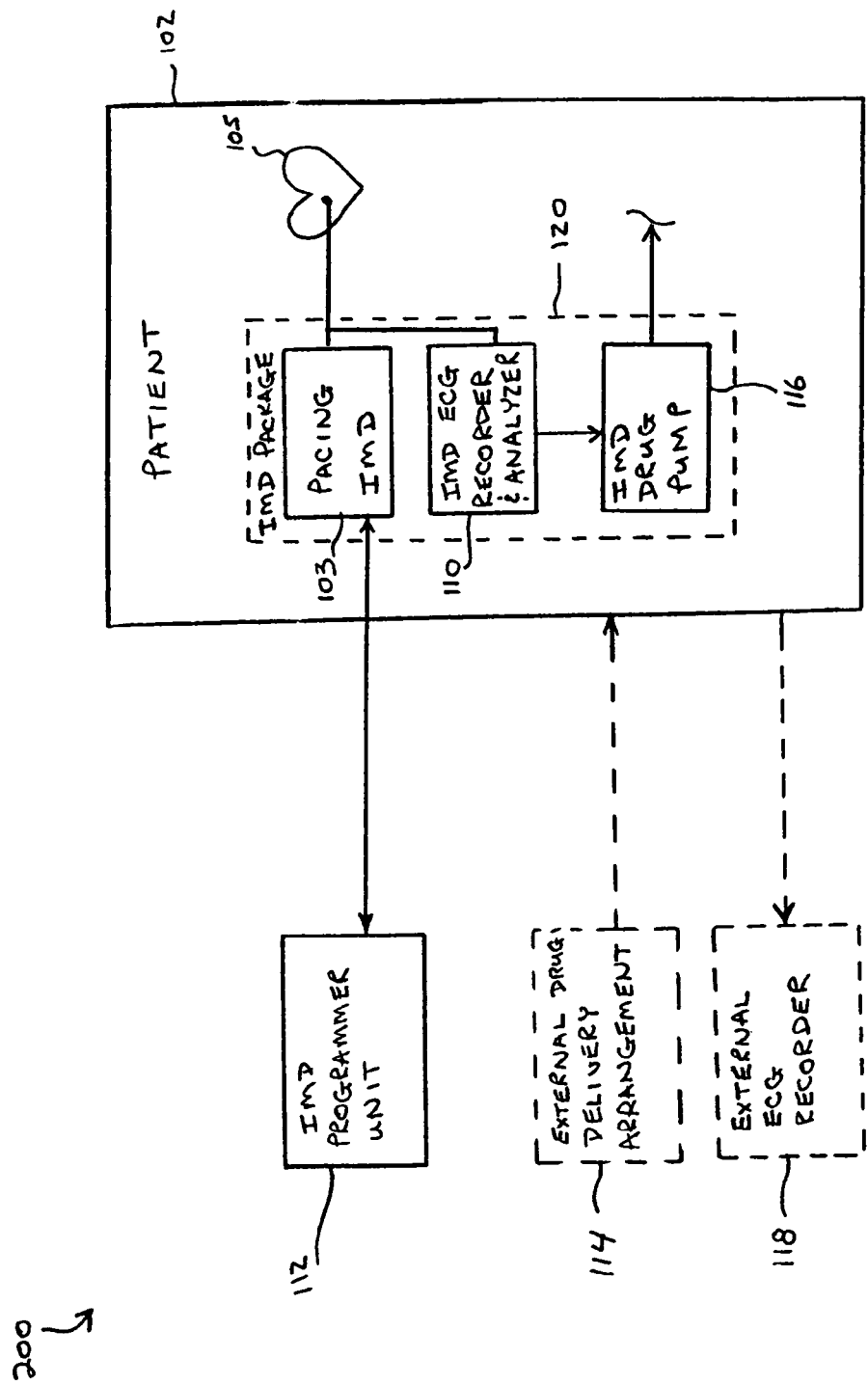
FIG. 2 is a block diagram of a system for preventing and/or terminating an atrial arrhythmia according to an example embodiment of the invention.

FIG. 2 is a block diagram of a system 200 for responding to an atrial arrhythmia using cardiac pacing and pharmaceutical therapies according to an example embodiment of the invention. In one example embodiment, the response is to arrest or terminate the atrial arrhythmia using cardiac pacing and the pharmaceutical therapies. In a more particular embodiment, the response is implemented internally within a patient via at least one IMD.

A patient 102 has a pacing implanted medical device (IMD) 103 that can detect an arrhythmia (irregular heartbeats) of a heart 105. According to one example implementation of the present invention, IMD 103 measures at least one electrocardiogram characteristic indicative of an atrial fibrillation, thereby detecting an atrial arrhythmia of the heart, and thereafter transmitting a warning signal to patient 102. Instead of, or in addition to, the traditional electrical cardioversion therapy, patient 102 chooses a pharmaceutical therapy via an available drug delivery arrangement, for example via an external drug delivery arrangement 114 (e.g., intravenously, orally, transdermally, intramuscularly, orally, nasally through spray, mask or misting bottle, occularly, inhalationally, among others) to terminate the atrial fibrillation. Through signaling, IMD effectively supervises drug therapy delivery to the patient. Heart conditions detectable by IMD 103 include, but are not limited to, ventricular fibrillation, tachycardia, bradycardia and eventual heart failure.

According to one example embodiment of the present invention, before patient 102 receives the pharmaceutical or drug therapy to terminate the atrial fibrillation, IMD 103 commences pacing a ventricle in heart 105 at a rate that exceeds, by a predetermined value, the spontaneous ventricular rate originally set by a physician as a means to prevent bradycardia associated with drug-induced proarrhythmia. The cardiac signals of heart 105 are monitored using an ECG (electrocardiogram) recorder. In one example implementation, the ECG recorder 118 is external to patient 102, as is conventional, the ECG traces being interpreted by a physician. In another example implementation, the ECG recorder is an IMD recorder and analyzer 110. IMD ECG recorder and analyzer 110 internally monitors and processes the patient 102's cardiac signals. According to a further example implementation, the functionality of pacing IMD 103 and IMD 110 are integrated into a single IMD package as indicated in FIG. 2 by dashed box 120. IMD drug pump 116 may or may not be integrated into IMD package 120, as is discussed further below.

IMD 110 monitors ECG tracings similar to tracing 100 in FIG. 1. IMD 110 collects and stores data from patient 102. In one example implementation, IMD 110 also includes application software that processes the cardiac signal data and generates data in various forms including Q-T prolongation data, Q-T interval variability data and ventricular ectopy data. IMD 110 is further adapted to process the cardiac signal data to determine whether conditions exist predictive of a possible onset of ventricular arrhythmia within patient 102, for example by measuring and comparing Q-T intervals.

During pacing by pacing IMD 103, IMD 110 continues monitoring cardiac signal data, for example measuring at least one Q-T interval of the heart and comparing the measured Q-T interval duration to a selected duration range. IMD 110 is adapted to determine that conditions predictive of a possible onset of ventricular arrhythmia exist whenever measured Q-T interval durations exceed the predetermined duration limits.

According to one example implementation of the present invention, IMD 110 signals patient 102 to not begin drug therapy responsive to a determination that conditions are detected that are predictive of a possible onset of ventricular arrhythmia. According to another example implementation of the present invention, IMD 110 prevents delivery of drug therapy responsive to a determination that conditions are detected that are predictive of a possible onset of ventricular arrhythmia. In a more particular example implementation, IMD 110 is adapted to prevent drug delivery from IMD drug pump 116 responsive to a determination by IMD 110 that conditions are detected that are predictive of a possible onset of ventricular arrhythmia, for example through comparison of a measured Q-T interval duration with a predetermined range for Q-T interval duration, drug therapy delivery being prevented responsive to the Q-T interval duration being out of range. IMD drug pump 116 is a stand-alone IMD, communicatively coupled to IMDs 103 and/or 110, or IMD package 120, in one example implementation. According to another example implementation, IMD drug pump 116 is integral to IMD package 120 and communicatively coupled to IMDs 103 and/or 110. Drug therapies are staged within patient 102 prior to onset of the atrial arrhythmia, for subsequent delivery by IMD drug pump 116.

If not prevented, or signaled to prevent, by IMD 110 (e.g., whenever measured Q-T interval durations are within the selected duration range), patient 102 begins receiving a medication from a drug delivery arrangement, for example external drug delivery arrangement 114, and/or IMD drug pump 116 communicatively coupled to IMD 110. Drug therapy delivery includes delivering an anti-arrhythmic drug, Ibutilide for example. As discussed earlier in the specification, the drug or medication is deliverable to patient 102 in various ways and with various drug delivery devices. Drug delivery devices include, but are not limited to, catheters, inhalers, face-masks, hypodermic needles, intravenous lines and the like.

IMD 110 concurrently monitors the patient's cardiac signals, measuring at least one Q-T interval of the heart. IMD 110 processes the cardiac signals to determine the effect that the delivered medication is having on patient 102 regarding arrhythmia status. For example, IMD 110 is adapted to determine that conditions predictive of a possible onset of ventricular arrhythmia exist by measuring Q-T interval durations outside a selected threshold duration range.

According to one example implementation of the present invention, IMD 110 signals patient 102, or an attending physician, to terminate drug therapy responsive to a determination that conditions are detected that are predictive of a possible onset of ventricular arrhythmia. According to another example implementation of the present invention, IMD 110 terminates delivery of drug therapy responsive to a determination that conditions are detected that are predictive of a possible onset of ventricular arrhythmia. In a more particular example implementation, IMD 110 is adapted to terminate drug delivery from IMD drug pump 116 responsive to a determination by IMD recorder 110 that conditions are detected that are predictive of a possible onset of ventricular arrhythmia. The patient's cardiac condition continues to be monitored by IMDs 103 and/or 110. In a related embodiment, patient 102 is given a warning or alert that patient 102 is in ventricular arrhythmia.

In one example embodiment of the present invention, while pacing the ventricles in response to the atrial arrhythmia, and prior to drug delivery, IMD 110 measures a Q-T interval of heart 105 and stores the pacing Q-T interval measurement as a control parameter. Drug delivery arrangement 114, and/or IMD drug pump 116, prevents drug therapy if the Q-T interval is at least as great as a threshold value. In a more particular example embodiment, drug therapy initiation is prevented if the Q-T interval prior to drug delivery is measured to be greater than 480 mS. If not prevented, the drug delivery arrangement 114, and/or IMD drug pump 116, subsequently delivers an anti-arrhythmic drug such as Ibutilide, to patient 102 after measuring the Q-T interval. According to another aspect of the present invention, drug therapy is prevented should prolongation of the Q-T interval occur in excess of a threshold prior to drug delivery.

While delivering the drug therapy, or shortly thereafter, IMD 110 measures at least one additional Q-T interval and denominates it as the drug therapy Q-T interval(s). Drug therapy is terminated if a drug therapy Q-T interval is measured to be greater than a drug therapy Q-T interval threshold. In a more particular example embodiment, drug therapy is stopped if the Q-T interval measured after initiation of drug therapy is measured to exceed 500 mS. According to another aspect, IMD 110 also compares the pacing Q-T interval (control parameter) with the drug therapy Q-T interval(s) to determine whether, and by what additional duration, the drug therapy Q-T interval(s) exceed the control parameter. After initiation of drug therapy delivery, Q-T interval prolongation exceeding a prolongation threshold, as detected by IMD 110, is indicative that conditions exist for the onset of ventricular arrhythmia. IMD 110 thereafter either warns patient 102, or terminates drug therapy.

In another embodiment of the invention, Q-T interval variability or dispersion is used as a measure of the effectiveness of the drug therapy in terminating an atrial fibrillation. While IMD 103 paces the ventricles in response to the atrial arrhythmia, and prior to drug therapy, IMD 110 measures variability in Q-T intervals (or dispersion) over a selected period, for example for a selected number of heartbeats. According to a more particular example implementation, the selected period is 20 heartbeats. IMD 110 measures dispersion, and stores a paced Q-T interval dispersion measurement as a dispersion control parameter. Subsequently, drug delivery arrangement 114, and/or IMD drug pump 116, delivers an anti-arrhythmic drug to patient 102. During drug therapy delivery, or shortly thereafter, IMD 110 again measures Q-T interval dispersion and classifies it as the drug therapy dispersion. IMD 110 measures dispersion over the period selected for measuring the dispersion control parameter, for example 20 heart beats, and refreshes the drug therapy dispersion measurement continuously. IMD 110 periodically compares the paced Q-T interval (control parameter) with the drug therapy Q-T dispersion. Drug therapy is terminated whenever the monitored drug therapy dispersion exceeds the dispersion control parameter by a selected quantity. According to a more particular implementation, IMD 110 signals for termination of, and/or terminates, drug therapy whenever the drug therapy dispersion exceeds the dispersion control parameter by fifty percent (50%) or more. Q-T interval dispersion provides an indication that conditions exist for the possible onset of ventricular arrhythmia, thereby mandating warning and/or termination of further drug therapy by IMD 110.

In yet another example embodiment, a high frequency of ventricular ectopy in the patient during a select period of time is used as a measure of the effectiveness of a drug therapy in terminating an atrial fibrillation. While IMD 103 paces the ventricles in response to the atrial arrhythmia, and prior to drug therapy, IMD 110 measures the frequency of ventricular ectopy over a selected period of time and stores a paced ventricular ectopy measurement as a ectopy control parameter. According to a more particular example implementation, the selected period is sixty (60) seconds. Subsequent to the paced ventricular ectopy measurement, drug delivery arrangement 114 and/or IMD drug pump 116 delivers an anti-arrhythmic drug to patient 102. During drug therapy delivery, or shortly thereafter, IMD 110 again measures the ventricular ectopy and classifies it as the drug therapy ventricular ectopy. IMD 110 compares the paced ventricular ectopy (control parameter) with the drug therapy ventricular ectopy, signaling to patient 102 that drug therapy should be terminated and/or terminating the drug therapy where the drug therapy ventricular ectopy exceeds the ectopy control parameter by a selected quantity. According to a more particular implementation of the present invention, IMD 110 signals and/or terminates drug therapy whenever the drug therapy ventricular ectopy exceeds the ectopy control parameter by fifty percent (50%) or more. A high frequency of ventricular ectopy provides an indication that conditions exist for the possible onset of ventricular arrhythmia, thereby mandating the warning and/or termination of drug therapy by IMD 110.

According to a further example embodiment of the present invention, IMD 110 alerts patient 102 that at least one ventricle is in arrhythmia after terminating the drug therapy delivery.

In the various embodiments described herein, IMD 110, IMD 103, IMD drug pump 116, and/or IMD package 120 are configured to communicate with each other. According to a more particular implementation, at least one of IMD 110, IMD 103, IMD drug pump 116, and IMD package is a discrete device and various telemetry communication techniques are used to communicatively couple any or all implanted devices to each other, or to external devices. Telemetry communication techniques include, but are not limited to, magnetic-field coupling, reflected impedance coupling and radio frequency (RF) coupling. For more information regarding magnetic-field coupling, reference may be made to U.S. Pat. No. 3,311,111 to Bowerand U.S. Pat. No. 3,805,796 to Terry et al., which is assigned to the assignee of the present invention and incorporated herein by reference. For more information regarding reflected impedance coupling, reference may be made to U.S. Pat. No. 4,223,679 to Schulman et al., which is assigned to the assignee of the present invention and incorporated herein by reference. For more information regarding RF coupling, reference may be made to U.S. Pat. No. 5,843,139 to Goedeke et al., which is assigned to the assignee of the present invention and incorporated herein by reference.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. An implantable system for delivering a therapy to a patient having a heart, comprising:
   an inplantable recorder and monitor adapted to monitor an electrical signal generated by the heart of the patient and identify a characteristic of the electrical signal generated by the heart of the patient indicative of an atrial arrhythmia a charateristic of the electrical signal generated by the heart predictive of a ventricular proarrhythmia; and
   a drug pump, operatively coupled to the implantable recorder and monitor, adapted to deliver a drug therapy to the patient based, at least in part, on the characteristic of the electrical signal indicative of the atrial arrhythmia and the characteristic of the electrical signal predictive of the ventricular proarrhythmia.

2. The implantable system of claim 1, wherein the drug pump is adapted to deliver the drug therapy to the patient based, at least in part, on the characteristic of the electrical signal indicative of the atrial arrhythmia and if the characteristic of the electrical signal predictive of the proarrhythmia indicates an unlikelihood of a future proarrhythmia.

3. The implantable system of claim 1 wherein the drug therapy comprises an anti-arrhythmia drug.

4. The implantable system of claim 3 wherein the anti-arrhythmia drug comprises Ibutilide.

5. The implantable system of claim 1 wherein the electrical signal generated by the heart defines, at least in part, a Q-T interval, and wherein the characteristic of the electrical signal predictive of the ventricular proarrhythmia is a time duration of the Q-T interval.

6. The implantable system of claim 5, wherein the time duration of the Q-T interval is outside of a selected range.

7. The implantable system of claim 5 wherein the time duration of the Q-T interval is at least 480 milliseconds.

8. The implantable system of claim 1 wherein the electrical signal generated by the heart defines, at least in part, a Q-T interval, and wherein the characteristic of the electrical signal predictive of the ventricular proarrhythmia is variability of time durations of individual ones of a plurality of Q-T intervals.

9. An implantable system for delivering a therapy to a patient having a heart, comprising:
  an implantable recorder and monitor adapted to monitor an electrical signal generated by the heart of the patient and identify a characteristic of the electrical signal generated by the heart of the patient indicative of an atrial arrhythmia and a characteristic of the electrical signal generated by the heart indicative of a ventricular proarrhythmia;
  a drug pump, operatively coupled to the implantable recorder and monitor, adapted to deliver a drug therapy to the patient based, at least in part, on the characteristic of the electrical signal indicative of the atrial arrhythmia; and
  an implantable pacing device, operatively coupled to the implantable recorder and monitor adapted to deliver a pacing therapy to the heart of the patient based, at least in part, on delivery of the drug therapy and on the characteristic of the electrical signal indicative of the ventricular proarrhythmia.

10. The implantable system of claim 9 wherein the drug therapy comprises an anti-arrhythmia drug.

11. The implantable system of claim 10 wherein the anti-arrhythmia drug comprises Ibutilide.

12. The implantable system of claim 9 wherein the electrical signal generated by the heart defines, at least in part, a Q-T interval, and wherein the characteristic of the electrical signal indicative of the ventricular proarrhythmia is a time duration of the Q-T interval.

13. The implantable system of claim 12 wherein the time duration of the Q-T interval is outside of a selected range.

14. The implantable system of claim 12 wherein the time duration of the Q-T interval is at least 480 milliseconds.

15. The implantable system of claim 9 wherein the electrical signal generated by the heart defines, at least in part, a Q-T interval, and wherein the characteristic of the electrical signal indicative of the ventricular proarrhythmia is a time duration difference of a Q-T interval prior to commencement of delivery of the drug therapy compared to a Q-T interval after commencement of delivery of the drug therapy.

16. The implantable system of claim 9 wherein the electrical signal generated by the heart defines, at least in part, a Q-T interval, and wherein the characteristic of the electrical signal indicative of the ventricular proarrhythmia is variability of time durations of individual ones of a plurality of Q-T intervals.

17. The implantable system of claim 9 wherein the electrical signal generated by the heart defines, at least in part, a frequency of ventricular ectopy, and wherein the characteristic of the electrical signal indicative of the ventricular proarrhythmia is a variability of a frequency of ventricular ectopy prior to commencement of delivery of the drug therapy compared to a frequency of ventricular ectopy after commencement of delivery of the drug therapy.

18. The implantable system of claim 17 wherein the variability of the frequency of ventricular ectopy after commencement of delivery of the drug therapy is at least fifty percent greater than the frequency of ventricular ectopy prior to commencement of delivery of the drug therapy.

19. An implantable system for delivering a therapy to a patient having a heart, comprising:
  an implantable recorder and monitor adapted to monitor an electrical signal generated by the heart of the patient and identify a characteristic of the electrical signal generated by the heart of the patient indicative of an atrial arrhythmia and a characteristic of the electrical signal generated by the heart predictive of a ventricular proarrhythmia;
  an implantable pacing device, operatively coupled to the implantable recorder and monitor adapted to deliver a pacing therapy to the heart of the patient based, at least in part, on the characteristic of the electrical signal indicative of the atrial arrhythmia and on the characteristic of the electrical signal predictive of the ventricular proarrhythmia; and
  a drug pump, operatively coupled to the implantable recorder and monitor, adapted to deliver a drug therapy to the patient based, at least in part, on the characteristic of the electrical signal indicative of the atrial arrhythmia and after commencement of delivery of the pacing therapy if the pacing therapy was delivered.

20. The implantable system of claim 19 wherein the drug pump is adapted to deliver the drug therapy to the patient based, at least in part, on the characteristic of the electrical signal indicative of the atrial arrhythmia and if the characteristic predictive of the proarrhythmia indicates an unlikelihood of a future proarrhythmia.

21. The implantable system of claim 19 wherein the drug therapy comprises an anti-arrhythmia drug.

22. The implantable system of claim 21 wherein the anti-arrhythmia drug comprises Ibutilide.

23. The implantable system of claim 19 wherein the electrical signal generated by the heart defines, at least in part, a Q-T interval, and wherein the characteristic of the electrical signal predictive of the ventricular proarrhythmia is a time duration of the Q-T interval.

24. The implantable system of claim 23 wherein the time duration of the Q-T interval is at least 480 milliseconds.

25. The implantable system of claim 19 wherein the electrical signal generated by the heart defines, at least in part, a Q-T interval, and wherein the characteristic of the electrical signal predictive of the ventricular proarrhythmia is variability of time durations of individual ones of a plurality of Q-T intervals.

26. An implantable system for delivering a therapy to a patient having a heart, comprising:
  an implantable recorder and monitor adapted to monitor an electrical signal generated by the heart of the patient and identify a characteristic of the electrical signal generated by the heart of the patient indicative of an atrial arrhythmia and a characteristic of the electrical signal generated by the heart indicative of a ventricular proarrhythmia;
  a drug pump, operatively coupled to the implantable recorder and monitor, adapted to deliver a drug therapy to the patient based, at least in part, on the characteristic of the electrical signal indicative of the atrial arrhythmia; and an implantable medical device, operatively coupled to the implantable recorder and monitor adapted to deliver a signal to the patient based, at least in part, on delivery of the drug therapy and on the characteristic of the electrical signal indicative of the ventricular proarrhythmia.

27. The implantable system of claim 26 wherein the drug therapy comprises an anti-arrhythmia drug.

28. The implantable system of claim 27 wherein the anti-arrhythmia drug comprises Ibutilide.

29. The implantable system of claim 26 wherein the electrical signal generated by the heart defines, at least in part, a Q-T interval, and wherein the characteristic of the electrical signal indicative of the ventricular proarrhythmia is a time duration of the Q-T interval.

30. The implantable system of claim 29 wherein the time duration of the Q-T interval is outside of a selected range.

31. The implantable system of claim 29 wherein the time duration of the Q-T interval is at least 480 milliseconds.

32. The implantable system of claim 26 wherein the electrical signal generated by the heart defines, at least in part, a Q-T interval, and wherein the characteristic of the electrical signal indicative of the ventricular proarrhythmia is a time duration difference of a Q-T interval prior to commencement of delivery of the drug therapy compared to a Q-T interval after commencement of delivery of the drug therapy.

33. The implantable system of claim 26 wherein the electrical signal generated by the heart defines, at least in part, a Q-T interval, and wherein the characteristic of the electrical signal indicative of the ventricular proarrhythmia is variability of time durations of individual ones of a plurality of Q-T intervals.

34. The implantable system of claim 26 wherein the electrical signal generated by the heart defines, at least in part, a frequency of ventricular ectopy, and wherein the characteristic of the electrical signal indicative of the ventricular proarrhythmia is a variability of a frequency of ventricular ectopy prior to commencement of deliver of the drug therapy compared to a frequency of ventricular ectopy after commencement of delivery of the drug therapy.

35. The implantable system of claim 34 wherein the variability of the frequency of ventricular ectopy after commencement of deliver of the drug therapy is at least fifty percent greater than the frequency of ventricular ectopy prior to commencement of delivery of the drug therapy.

* * * * *